United States Patent
Poot et al.

(12)

(10) Patent No.: US 6,291,203 B1
(45) Date of Patent: Sep. 18, 2001

(54) CYANINE DYES THAT STAIN CELLS AND MITOCHONDRIA

(75) Inventors: Martin Poot, Seattle, WA (US); Fei Mao, Eugene, OR (US)

(73) Assignee: Molecular Probes, Inc., Engene, OR (US)

( * ) Notice: Subject to any disclaimer, the term of this patent is extended or adjusted under 35 U.S.C. 154(b) by 0 days.

(21) Appl. No.: 09/266,697

(22) Filed: Dec. 3, 1998

Related U.S. Application Data (63) Continuation of application No. 08/555,467, filed on Nov. 13, 1995, now abandoned.

(51) Int. Cl.[7] .................................................. G01N 1/30
(52) U.S. Cl. .......................................... 435/40.5; 546/165
(58) Field of Search .................................. 435/4.34, 40.5; 436/172, 800; 546/165

(56) References Cited

U.S. PATENT DOCUMENTS

| | | | | |
|---|---|---|---|---|
| 3,623,882 | * | 11/1971 | Gotze et al. | 96/137 |
| 3,890,155 | * | 6/1975 | Nakamura et al. | 96/137 |
| 3,988,513 | * | 10/1976 | Matsuyama et al. | 427/43 |
| 4,336,321 | * | 6/1982 | Kanada et al. | 430/234 |
| 5,041,366 | * | 8/1991 | Asano et al. | 430/567 |

FOREIGN PATENT DOCUMENTS

| | | | |
|---|---|---|---|
| 1923992 | * | 11/1970 | (DE) . |
| 1510234 | * | 1/1968 | (FR) . |

OTHER PUBLICATIONS

Bartnick R. Synthesis of New Trimethinecyanine Dyes . . . Polish J of Applied Chemistry 37(1–2)119–25, 1993.*
Stezenko, T. .Cyanine Dyes, Derivatives . . . Ukr Khim Zh, vol. 27, 237–240, 1961.*
Wang L. Journal of Wuhan Univ. 2:73–77, Feb. 1991.*
Stetsenko A. V. Benzimidocyanines. Ukr Khim Zh 43(1)57–61, Jan. 1977.*

* cited by examiner

*Primary Examiner*—Ralph Gitomer
(74) *Attorney, Agent, or Firm*—Allegra J. Helfenstein (57) ABSTRACT

The present invention relates to the use of positively-charged unsymmetrical cyanine dyes, including novel unsymmetrical cyanine dyes, to stain cells and selectively stain intracellular organelles, with particular advantages in staining mitochondria. The dyes are generally weakly fluorescent in aqueous solution but highly fluorescent in cells and organelles, typically staining cells or mitochondria with a green fluorescence. The dyes stain mitochondria in both live and dead cells, and are retained in mitochondria even where the cells are treated with solvents that permeabilize cell and mitochondrial membranes. Mitochondria or cells stained according to this method are optionally stained with an additional detection reagent, such as a labeled antibody, labeled oligonucleotide, fluorogenic enzyme substrate, or other indicator for a specific cellular component or substructure, including another unsymmetrical cyanine stain of the same or different class.

22 Claims, 4 Drawing Sheets

CYANINE DYES THAT STAIN CELLS AND MITOCHONDRIA

The present application is a Continuation Application of U.S. application Ser. No. 08/555,467, filed Nov. 13, 1995, now abandoned.

FIELD OF THE INVENTION

The invention relates to the fluorescent staining of cells with unsymmetrical cyanine dyes (including novel dyes) that can be used to selectively stain cellular membranes and organelles, especially mitochondria.

BACKGROUND

Fluorescent dyes are known to be particularly suitable for biological applications in which a highly sensitive detection reagent is desirable. Dyes that are able to preferentially bind to a specific biological ingredient in a sample enable the researcher to determine the presence or quantity of that specific ingredient. In addition, specific cellular structures can be monitored with respect to their spatial and temporal distribution in diverse environments.

Mitochondria are the intracellular organelles that perform the aerobic mode of metabolic energy generation in eukaryotic cells. Their abundance varies as a function of cell type, cell-cycle stage and proliferative state. There is a need in biology to detect and observe mitochondria particularly in cells, as a specific application or in conjunction with additional labeling of other components under study. Due to the strong proton gradient across the mitochondrial membrane, a variety of substances that possess a cationic charge have been found to selectively localize within functioning mitochondria. Under the proper conditions, this property has been used to localize a variety of fluorescent dyes within mitochondria for use in imaging (Haugland, MOLECULAR PROBES HANDBOOK OF FLUORESCENT PROBES AND RESEARCH CHEMICALS Set 30 (1992) (hereinafter "1992 HANDBOOK") incorporated by reference).

There are several "xanthylium" dyes that have proven useful for mitochondrial labeling. The fluorescent dyes tetramethylrosamine, rhodamine 123 and rhodamine 6G are readily sequestered in mitochondria, where localization of the dyes is a function of membrane potential. These mitochondrial stains have been used in conjunction with flow cytometry to sort and/or analyze cells. See, for example Rothe et al., JOURNAL OF IMMUNOLOGICAL METHODS 138, 133 (1991). These xanthylium stains for mitochondria, however, share common disadvantages. The xanthylium dyes are essentially fluorescent in any medium, resulting in problems with background fluorescence. Rhodamine 123, which is widely used because of its green fluorescence, is also the least photostable. Furthermore, the green fluorescent dye has significant spectral overlap with commonly used red fluorescent dyes, making multicolor assays more difficult to resolve.

In addition, the cationic xanthylium dyes are sequestered in the mitochondria in an equilibrium process, and transporting stained cells to fresh medium typically results in the loss of mitochondrial staining, as the stains are lost through leaching into the medium. Attempts to fix stained cells generally results in cell death, the loss of mitochondrial potential, and therefore the loss of mitochondrial staining. This is a drawback for researchers wishing to investigate mitochondrial function or viability in pathogenic species, who must choose between the very poor staining procedures available for fixed cells, or the additional hazards and costs associated with handling live pathogens.

These difficulties were partially overcome by the introduction of a family of xanthylium mitochondrial stains that are substituted by a reactive alkylating group, typically a halomethyl, that are well retained after fixation and permeabilization of the cell. The retention of staining also allows the use of other labeling techniques, including immunocytochemical staining of intracellular antigens and in situ hybridization in combination with mitochondrial staining, as many of these techniques require permeabilization of the cell membranes to allow the bulky labeling agents to enter the cellular space. These xanthylium dyes are described in U.S. Pat. No. 5,459,268 to Haugland et al. (1995) and U.S. Pat. No. 5,686,261 to Zhang et al. (1997) (incorporated by reference). Like the xanthylium dyes described above, these dyes are essentially fluorescent in aqueous medium. The green fluorescent dyes of this family also share the disadvantageous spectral overlap with commonly used red dyes.

Figure 3:
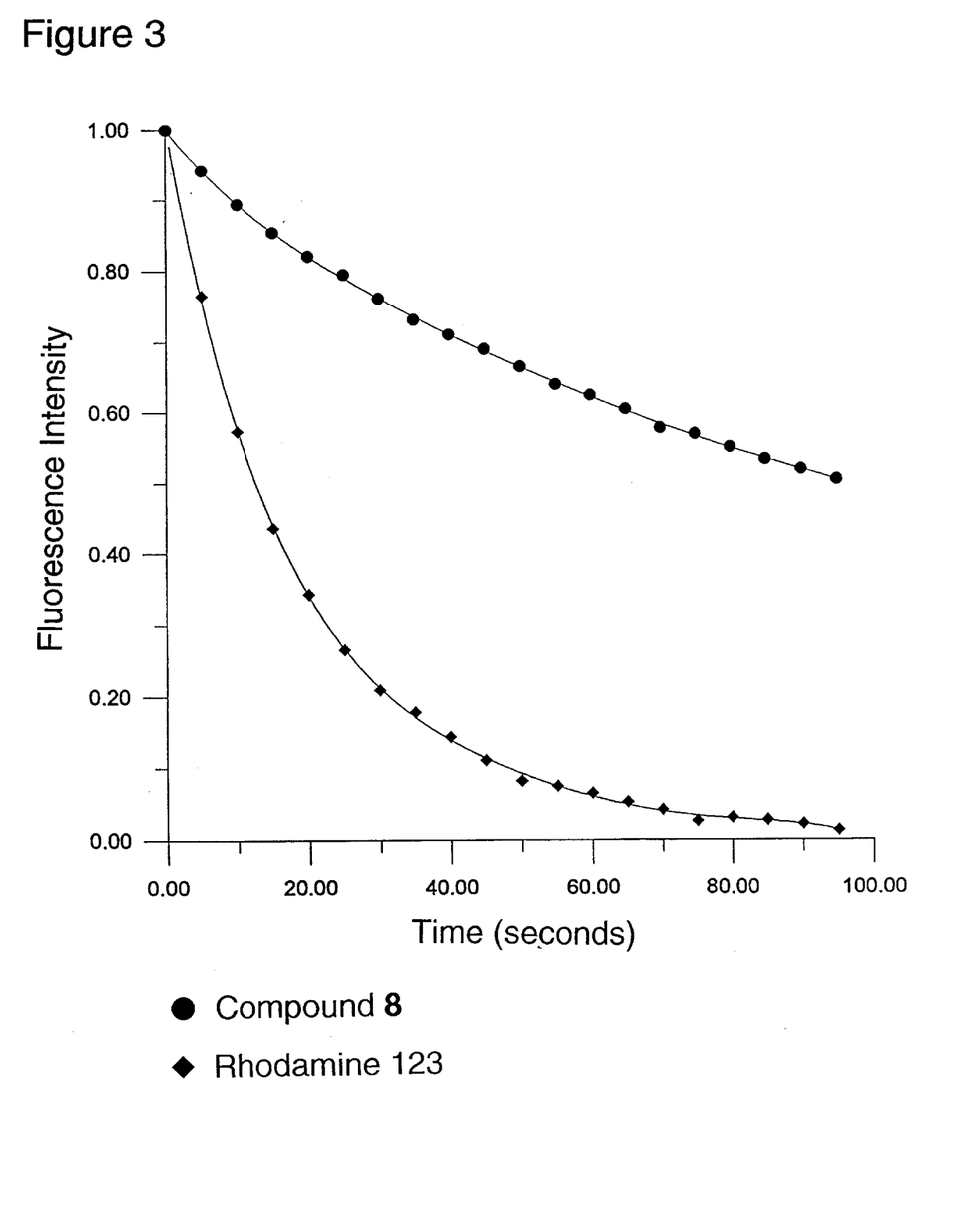
FIG. 3: A comparison of photostability between Compound 8 and rhodamine 123, as described in Example 18.

The cyanine dyes of the present invention, with particular advantages in the staining of mitochondria, have advantageous spectral properties. Whereas xanthylium dyes and most known mitochondrial stains are intrinsically quite fluorescent, the dyes of the invention are very weakly fluorescent in aqueous solution but are enhanced by incorporation into a lipophilic environment (FIG. 4), which improves the quality of staining lipophilic compartments by improving the signal to noise ratio. The fluorescence emission of the subject dyes can be tuned from the blue-green to the far red region of the visible spectrum, and the green fluorescent dyes have less spectral overlap with commonly used red fluorophores. Additionally, the dyes of the invention are substantially more photostable than the xanthylium dyes previously used to stain mitochondria (FIG. 3). Dyes of the present invention with lower alkyl substituents are well retained in mitochondria, allowing cells under study to be washed and placed in fresh media without significant loss of staining. Where further retention is required, dye embodiments of the present invention possessing a haloalkyl substituent generally yield mitochondrial staining that is more resistant to fixation and permeabilization.

The symmetrical lipophilic carbocyanine dye $DiOC_7(3)$ (3,3'-diheptyloxacarbocyanine iodide) has been reported to be useful as a stain for mitochondria of plant cells, e.g. Liu, et al., PLANT PHYSIOL. 84, 1385 (1987). Mitochondria stained with this carbocyanine dye, however, are more susceptible to dye removal by solvents and do not retain staining if the membrane potential is destroyed. DiO derivatives similar to $DiOC_7(3)$ do not selectively stain the mitochondria of mammalian cells (e.g. $DiOC_6(3)$ and $DiOC_5(3)$, which are known to stain the endoplasmic reticulum). Another symmetrical cyanine dye that has been used to stain mitochondria is JC-1 (5,5', 6,6'-tetrachloro-1,1', 3,3'-tetraethylbenzimidazolylcarbocyanine iodide). The dye tends to form so-called-J-aggregates within mitochondria that have a red fluorescence emission, and the fluorescence of the dye changes reversibly from green to greenish orange as the mitochondrial membrane becomes more polarized (U.S. Pat. No. 5,169,788 to Chen, Steele & Smiley, issued Dec. 8, 1992). This characteristic of JC-1, while advantageous for some applications, can result in non-specific red fluorescent staining in the cytoplasm and can obscure other dyes in multicolor applications. The dyes of the present invention do not form these aggregates, and the wavelength of fluorescence emission is essentially constant throughout the staining process. The dyes of the invention are less susceptible to removal by solvents after staining and will even stain mitochondria after they have been treated with solvents that fix and permeabilize cell membranes.

Other retention methods have been utilized to make cyanine dyes fixable. Schneider et al. (HISTOCHEMISTRY 101, 135 (1994)) incorporate a diazirine ring into the lipophilic chain of a carbocyanine dye. Similarly, carbocyanine dyes having the photoaffinity label 4-azido-2-nitrophenyl as a substituent are described by Hahn et al. (J. HISTOCHEM. CYTOCHEM. 41, 631 (1993)). However, the use of the above photoaffinity labels requires the additional step of photolysis before the subject cells are fixed. The photolysis also requires additional specialized equipment and exposes the sample to UV irradiation and heat that may damage the cells or tissues under examination.

SUMMARY OF THE INVENTION AND DESCRIPTION OF PREFERRED EMBODIMENTS

The present invention relates to the use of positively-charged unsymmetrical cyanine dyes, including novel unsymmetrical cyanine dyes, to stain cells and selectively stain intracellular organelles, with particular advantages in staining mitochondria. The dyes are generally weakly fluorescent in aqueous solution but highly fluorescent in cells and organelles, typically staining cells or mitochondria with a green fluorescence. The dyes stain mitochondria in both live and dead cells, and are retained in mitochondria even where the cells are treated with solvents that permeabilize cell and mitochondrial membranes. Mitochondria or cells stained according to this method are optionally stained with an additional detection reagent, such as a labeled antibody, a chromogenic or fluorogenic enzyme substrate, a labeled oligonucleotide, or other indicator for a specific cellular component or substructure, including another unsymmetrical cyanine stain of the same or different class.

Description of the Dyes

The dyes of the present invention are unsymmetrical cyanine dyes having a positive charge that, under appropriate conditions, are selectively sequestered in mitochondria.

The preferred dyes of the present invention are described by the formula

The nitrogen substituents $R^1$, $R^2$ and $R^3$ are independently a linear hydrocarbon group having 1–22 carbons that is a saturated or unsaturated aliphatic chain that optionally contains a phenylene moiety and that is optionally and independently substituted by one or more H or halogen, or an A moiety as described below. Typically, the hydrocarbon groups at $R^1$, $R^2$ and $R^3$ have fewer that 10 carbons (independently of A) for dyes used in staining mitochondria; more typically, the hydrocarbon groups have fewer than 6 carbons (independently of A).

The benzimidazolium ring substituents $R^4$, $R^5$, $R^6$ and $R^7$ are independently H, halogen, CN, or phenyl; or an alkyl group having 1–22 carbons that is optionally and independently substituted by one or more H or halogen, or an A moiety (as below); or any of such ring substituents is independently an A moiety; or any of such ring substituents is independently —$OR^{12}$ or —$SR^{12}$, where $R^{12}$ is an alkyl group having 1–6 carbons, or 1–2 alicyclic, heteroalicyclic, aromatic or heteroaromatic rings, containing 1–2 heteroatoms, wherein the heteroatoms are N, O, or S; or any two adjacent substituents of $R^4$, $R^5$, $R^6$ and $R^7$ combine to form a single fused benzo substituent. Typically, no more than two of $R^4$, $R^5$, $R^6$ and $R^7$ are nonhydrogen. The alkyl portion of any ring substituents are typically lower alkyl (1–6 carbons), more typically having 1–3 carbons. Where any of $R^4$, $R^5$, $R^6$ and $R^7$ is not hydrogen or part of a fused ring, it is preferably trifluoromethyl, a halogen or —$OR^{12}$. To simplify the synthesis of the materials, preferably $R^5=R^6$ and $R^4=R^7$. Preferably, $R^5$ and $R^6$ are Cl.

Like the benzimidazolium ring substituents described above, the benzazole ring substituents $R^8$, $R^9$, $R^{10}$ and $R^{11}$ are independently H, halogen, CN, or phenyl; or an alkyl group having 1–22 carbons that are optionally and independently substituted by one or more H or halogen, or an A moiety (as below); or any of such ring substituents is independently an A moiety; or any of such ring substituents is independently —$OR^{12}$ or —$SR^{12}$, where $R^{12}$ is an alkyl group having 1–6 carbons, or 1–2 alicyclic, heteroalicyclic, aromatic or heteroaromatic rings, containing 1–2 heteroatoms, wherein the heteroatoms are N, O, or S; or any two adjacent substituents of $R^8$, $R^9$, $R^{10}$ and $R^{11}$ combine to form a single fused benzo substituent. Fused ring benzo substituents, where present, are more common on the benzazolium portion of the dye molecule. Typically, no more than one of $R^8$, $R^9$, $R^{10}$ and $R^{11}$ is nonhydrogen. Preferably each of $R^8$, $R^9$, $R^{10}$ and $R^{11}$ is hydrogen. The alkyl portion of any ring substituents are typically lower alkyl (1–6 carbons), more typically having 1–3 carbons. Where any of $R^8$, $R^9$, $R^{10}$ and $R^{11}$ is not hydrogen or part of a fused ring, it is preferably halomethyl, a halogen or —$OR^{12}$.

Each alkyl group of $R^1$, $R^2$, $R^3$, $R^4$, $R^5$, $R^6$, $R^7$, $R^8$, $R^9$, $R^{10}$ and $R^{11}$ is independently and optionally substituted by one or more H or halogens (F, Cl, Br, or I) at any position on the alkyl, such that such alkyl group is haloalkyl, where haloalkyl means an alkyl substituted by one halogen or more than one halogens, which are the same or different, and includes perhaloalkyl. Preferred halogens are Cl, Br and F. Typically, all halogens on a given alkyl group are the same.

Each such alkyl group is also optionally and independently substituted by an A moiety. The A moiety has the formula —L—$CR^aR^b$—X, where L is a single covalent bond, or L is a carbonyl (—C=O—), or L is a phenylene (—$C_6H_4$—). Preferably L is a carbonyl or phenylene. X is halogen or X is a sulfonate ester —$OSO_2R^c$, where $R^c$ is an alkyl with 1–6 carbons, a perfluoroalkyl with 1–6 carbons, phenyl, or $R^c$ is a phenyl substituted one or more times by an alkyl with 1–6 carbons, perfluoroalkyl with 1–6 carbons, H, Cl, Br, I, $NO_2$ or CN. Typically, X is halogen (preferably Cl). The substituents $R^a$ and $R^b$ are independently H, halogen, or $CH_3$. Typically $R^a$ and $R^b$ are H or halogen, except that when X is a sulfonate ester, neither $R^a$ nor $R^b$ are halogen. Alternatively, the A moiety is a maleimido ($-NC_4H_2O_2$) or haloacetamido ($-NH(C=O)-CH_2Z$) where Z is Cl, Br or I. Alternatively, L is a phenylene and $-CR^aR^b-X$ is $C_3$.

While all of the dyes of the invention possess excellent retention within mitochondria, those embodiments that possess an A moiety are retained in mitochondria even longer than embodiments without the group A substituent. In one embodiment, the dye contains at least one A moiety, which is contained on $R^1$, $R^2$, $R^3$, $R^4$, $R^5$, $R^6$, $R^7$, $R^8$, $R^9$, $R^{10}$, or $R^{11}$. Typically, the A moiety is substituted only on the group of substituents selected from $R^1$, $R^2$ and $R^3$. In one embodiment of the invention, each of $R^1$ and $R^2$ is substituted by one A moiety.

W of the benzazole ring is selected from O, S, Se, Te or $CR^{13}R^{14}$ where $R^{13}$ and $R^{14}$, which may be the same or different, are independently alkyl groups having 1–6 carbons, or $R^{13}$ and $R^{14}$ taken in combination complete a five or six membered saturated ring. Preferably, W is O, S, or $CR^{13}R^{14}$.

The variable n is an integer that has any value from 0 to 3, yielding a bridge moiety that is a monomethine, trimethine, pentamethine or heptamethine bridge, respectively. The spectral properties of the dye are highly dependent upon the length of the bridge moiety, with the excitation and emission wavelengths shifting to longer wavelengths with the addition of each alkenyl segment. Typically n is 1, commonly yielding a green fluorescent mitochondrial stain. Dyes having n=0 will have very short wavelength fluorescence properties, while dyes having n=2 or more will exhibit progressively longer wavelength excitation and emission. Preferably n=0–2, more preferably n=1. The judicious selection of polymethine bridge length, in conjunction with selection of bathochromic substituents at the benzazolium and benzimidazolium portions of the dye allows the researcher to tailor the spectral properties of the resulting dye over a wide range of wavelengths.

To achieve selective localization of the dyes of the present invention by the mitochondria requires that the overall charge of the unsymmetrical cyanine dye be positive. The necessary positive charge present on the cyanine dyes of the invention is balanced by the presence of a biologically compatible counterion, which is indicated by the symbol $\Psi^-$. As used herein, a biologically compatible counterion is not toxic as used, and does not have a substantially deleterious effect on biomolecules. Examples of $\Psi^-$ include, among others, chloride, bromide, iodide, sulfate, alkanesulfonate, arylsulfonate, phosphate, perchlorate, tetrafluoroborate, tetraphenylboride, nitrate and anions of aromatic or aliphatic carboxylic acids. Preferred $\Psi^-$ counterions are chloride, iodide, perchlorate and various sulfonates.

Synthesis

Cyanine dyes have been widely used in photographic and textile industries, and their synthesis is well documented (Hamer et al., "Cyanine Dyes and Related Compounds," The Chemistry of Heterocyclic Compounds, vol. 18, A. Weissberger, Ed., Interscience, New York (1964)). The procedures described herein offer a general approach to the synthesis of the dyes in this invention. In brief, synthesis of the dyes is accomplished by combining the three constituent parts of the dyes: the benzimidazolium moiety, the methine or polymethine moiety, and the benzazolium moiety, each of which is either commercially available or is readily prepared synthetically.

The Benzimidazolium Moiety

Synthesis of the benzimidazolium portion of the dyes of the invention typically starts with an appropriately substituted 1,2-phenylenediamine, followed by treatment of the diamine with triethylorthoacetate in the presence of a catalyst, typically toluenesulfonic acid, to form the 2-methylbenzimidazole derivative. Benzo-substituted benzimidazoles are prepared from a 1,2-naphthalenediamine or 2,3-naphthalenediamine. Alkylation at the nitrogen atoms of the 2-methylbenzimidazole intermediate is carried out by heating the derivative with an alkylating agent $R^1$—Z or $R^2$—Z where $R^1$ and $R^2$ are alkyl groups of the properties described before, or groups that can be subsequently converted to permitted substituents, and Z is an electronegative group that typically becomes the counterion, $\Psi^-$, for the resulting dye. Alkylation can be carried out stepwise so that $R^1$ and $R^2$ can be different alkyl groups. The resulting benzimidazolium precursor has the general structure The Benzazolium Moiety A wide variety of benzazolium intermediates for use in preparing photographic dyes have been described, in particular by Brooker and his colleagues (Brooker, et al., J. AM. CHEM. SOC., 64, 199 (1942)). These synthetic precursors have the common structure:

If W is O, the precursor compound is a benzoxazolium; if W is S it is a benzothiazolium; if W is Se it is a benzoselenazolium; if W is Te, it is a benzotellurazolium; and if W is $CR^{13}R^{14}$ (as described previously) then it is an indolinium derivative. Commonly $R^{13}$ and $R^{14}$ are both methyl. However, methods for preparing compounds where $R^{13}$ and $R^{14}$ are not methyl are known. The commercial availability of suitable starting materials and relative ease of synthesis make compounds with X=O or S the preferred intermediates. Benzo substituted benzazolium precursors (naphthazole compounds) are commercially available or are readily prepared by published procedures.

$R^3$ is optionally incorporated in the benzazole precursor prior to ring cyclization but $R^3$ is usually obtained by alkylation of the parent heterocycle with an alkylating agent $R^3$—Z, as described above.

K is a substituent whose nature is determined by the synthetic method used to couple the benzazolium precursor to the benzimidazolium precursor. Depending on the compound desired and the synthetic method used, K is either methyl, or K is a leaving group. When n=0, K on one of the aromatic precursors is methyl, and a leaving group on the other, usually alkylthio (commonly methylthio) or chloro, bromo or iodo. In the synthetic precursors shown above, one precursor contains a methyl group and the other contains K, but either precursor could contain K. When n=1, 2 or 3, K is methyl on both precursors. Only when K is methyl is any part of K incorporated in the final compound.

Synthesis of the Cyanine Dyes

The unsymmetrical cyanine dyes are normally synthesized by first reacting the coupling agent with the benzazolium moiety to form a reactive intermediate that is then coupled to the benzimidazolium moiety in the presence of a base, usually N,N-diisopropylethylamine in combination with acetic anhydride. Alternatively, the benzimidazolium moiety may react with the coupling agent first, followed by coupling with the benzazolium moiety in the presence of N,N-diisopropylethylamine and acetic anhydride. The polymethine bridging moiety, which has the general formula —(CH=CH)$_n$—CH=, usually originates from the coupling agent used in the dye construction: e.g. N,N'-diphenylformamidine yields n=1; malonaldehyde bis (phenylimine) hydrochloride yields n=2; and glutaconaldehyde dianil hydrochloride yields n=3.

Cyanine dyes having a monomethine bridge are typically synthesized by treating a derivative of 2-alkylthiobenzimidazolium with one equivalent of a 2-methylbenzazolium derivative in the presence of a base.

The 2-alkylthiobenzimidazolium salt is typically synthesized by treating a 1,2-phenylenediamine derivative, which is either commercially available or can be readily prepared, with one equivalent of thiophosgene in the presence of a base, followed by the alkylations of the nitrogens and sulfur atoms of the 2-mercaptobenzimidazole derivative. In this case it is usually synthetically easier to have the two nitrogen and the sulfur atoms substituted by the same alkyl group by using a large excess of an alkylating agent.

If necessary, the counterion $\Psi^-$ is exchanged by means well known in the art, including but not limited to ion exchange chromatography, precipitation in the presence of a large excess of a salt of $\Psi^-$ or selective extraction or precipitation of the salt with an organic solvent.

Use of the Dyes of the Invention to Stain Cells and Organelles

The dyes of the present invention are utilized by preparing a labeling solution of the dye that is combined with a biological sample for a time sufficient to produce a detectable fluorescent response. Observing or analyzing the pattern of the fluorescent response in the sample gives useful information about the sample. Organelles in the sample are optionally contained in cells or are isolated organelles (i.e. not incorporated in a cell).

Preparation of a Labeling Solution

The pure dyes generally have low solubility in water. Typically a stock solution is prepared by weighing out a known mass of the pure reagent and dissolving the reagent in an organic solvent. Preferred organic solvents are DMSO, dimethylformamide, acetone, acetonitrile, dioxane, tetrahydrofuran and other nonhydroxylic, completely water-miscible solvents. The stock solutions are protected from light at all times. The labeling solution is prepared by diluting an aliquot of the stock solution into aqueous buffer to the desired labeling concentration.

In general, the amount of dye in the labeling solution is the minimum amount required to yield detectable staining in the sample, without significant background fluorescence or undesired staining of cellular structures. The amount of reagent required for staining eukaryotic mitochondria depends on the sensitivity required for staining of intracellular vs. cell-free mitochondria, the number of cells present, and the permeability of the cell membrane to the reagent. In the case of staining of tissues, the amount of reagent required may also vary with the accessibility of the reagent to the cells in the tissue. The required concentration for the labeling solution is determined by systematic variation in labeling concentration until a satisfactory level of fluorescent labeling is accomplished.

The amount of fluorescent cyanine dye required for staining mitochondria in live mammalian cells, without staining of other organelles or membranes, is generally less than 1 $\mu$M; typically less than 500 nM, more typically about 20 nM to about 100 nM. At higher concentrations of stain, background fluorescence or non-specific cellular staining may occur in live cells, but resolution of mitochondria after fixation is improved. At staining concentrations of between 200 nM and 800 nM, the mitochondria are brightly stained after fixation, with little or no background. Staining of isolated (cell-free mitochondria) will typically require lower concentrations of dye. Dye concentrations of less than 1 $\mu$M are typically used for staining dead or previously fixed cells; more typically, dye concentrations between 50 nM and 500 nM are used, preferably 100–200 nM.

Low concentrations of dye will require longer incubation times for equivalent fluorescent brightness to be reached. Typically cells incubated in 10–30 nM labeling solution will require about 1 to 3 hours to reach an arbitrary level of fluorescent staining that is reached in about 15–20 minutes using a 100 nM labeling solution. Dye concentrations between 100 nM and 500 nM give good staining of mitochondria within about 10–20 minutes, in dead cells or isolated in solution. The exact concentration of stain to be used is dependent upon the experimental conditions and the desired results and optimization of experimental conditions is required to determine the best concentration of stain to be used in a given application.

Staining the Sample

The sample optionally comprises cells or cell-free organelles or components thereof. Typically the sample contains whole mitochondria or isolated components of mitochondria, or the sample contains cells that contain mitochondria. Any cells that contain mitochondria can be used, including but not limited to, fresh or cultured cells, cell lines, cells in biological fluids, cells in tissue or biopsy, and yeast cells.

Following preparation of the labeling solution, the solution is combined with the sample being analyzed. The dyes of the present invention are membrane permeant, and can be introduced into live cells, dead cells, or isolated organelles by incubation with the labeling solution. Any other treatment that will permeabilize the plasma membrane, such as electroporation, shock treatments or high extracellular ATP can be used to accelerate introduction of the dye into the cellular cytoplasm. Preferably the dye is introduced in to the cell or cells by incubation in the labeling solution. Microinjection of dye solution is used when analysis of mitochondrial function of a single cell is desired, within a colony of other sample cells. Once the mitochondria of the sample are stained by the dyes of the invention, the mitochondria retain the staining even after the sample is washed and placed in fresh media (Example 19). Satisfactory mitochondrial visualization is possible without washing.

A number of reagents and conditions are known to effect the mitochondrial membrane potential and the metabolism by mitochondrial enzymes. Mitochondrial uncouplers such as 2,4-dinitrophenol, KCN, CCCP (carbonyl cyanide m-chlorophenylhydrazone), and with carbonyl cyanide p-trifluoromethoxyphenyl- hydrazone (FCCP) depress the mitochondrial membrane potential, which generally results in the decreased uptake of cationic dyes. Cells pretreated with FCCP and subsequently stained with Compound 17 showed some 50% reduction in fluorescence by CCCD-camera assisted microscopy compared to cells stained without FCCP treatment. Cells treated with 20 μM CCCP, rotenone, or antimycin, however, showed essentially no sensitivity toward pretreatment with the inhibitors of mitochondrial function (Example 25), unlike most other known mitochondrial stains, indicating that the staining is not driven by the mitochondrial membrane potential.

The dyes of the present invention are generally non-toxic to living cells and mitochondria. Cells incubated in 100 nM dye solution for 48 hours show normal morphology and show no loss of cell membrane integrity when stained with propidium iodide. Stained cells have undergone cell division, producing daughter cells that also possess stained mitochondria.

Before or after staining, the cells are optionally treated with solvents to fix, and optionally permeabilize, the membranes. A number of fixatives and fixation conditions are suitable for practicing this invention. Useful fixatives include, but are not limited to, formaldehyde, paraformaldehyde, cold methanol, cold ethanol, and 3:1 methanol:acetic acid. Typically, cell fixation is accomplished by incubating in a 3.7% solution of paraformaldehyde for about 15–30 minutes.

Figure 1:
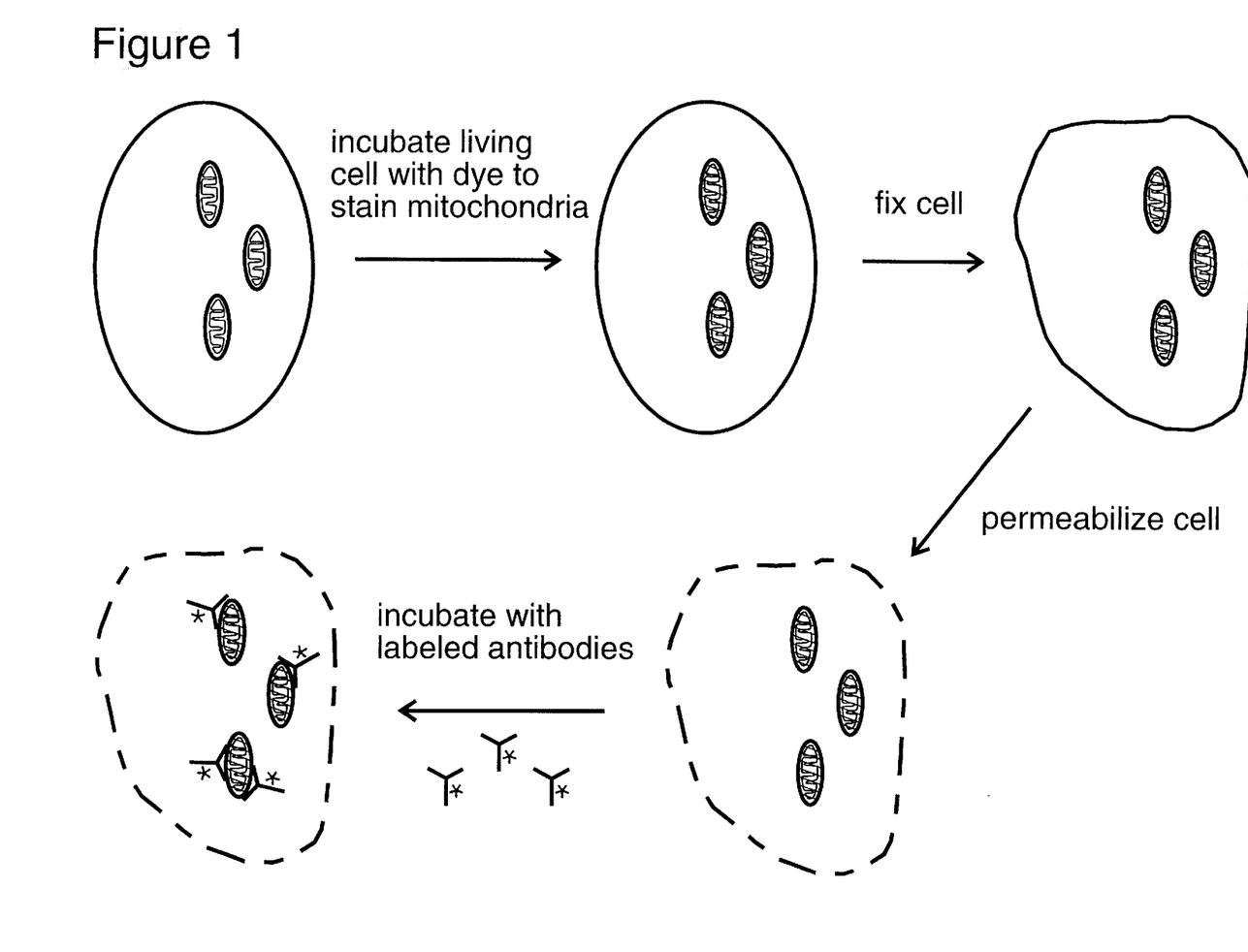
FIG. 1: Staining of mitochondria in a cell is followed by fixation, permeabilization, and incubation with an additional detection reagent while retaining the mitochondrial stain (Example 22).

Fixation is optionally followed or accompanied by permeabilization, such as with acetone, ethanol, DMSO or various detergents. Permeabilization is utilized to allow bulky additional detection reagents to enter the cellular space that would ordinarily be impermeant with respect to the cellular membrane (FIG. 1). A large variety of fixatives, fixation conditions, and permeabilization agents are known in the art, and other methods of fixing or permeabilizing sample cells in conjunction with the stains of the present invention will be obvious to one of ordinary skill. Mitochondria stained by dyes of the present invention containing an A moiety retain some fluorescent staining even after fixation and permeabilization.

Additional Detection Reagents

The use of stains according to the present invention is optionally combined with the use of an additional detection reagent. An additional detection reagent is a reagent that produces a detectable response due to the presence of a specific cell component, intracellular substance, or cellular condition. One or more additional detection reagents may be used in conjunction with the stains of the present invention, before or after fixation and/or permeabilization. The additional detection reagent may be used to stain the entire cell, or a cellular substructure by selection of an appropriate additional detection reagent with the desired degree of selectivity, such as a labeled antibody, labeled oligonucleotide, an enzymic activity, or other indicator for a specific cellular component or substructure, e.g. a stain that is selective for the cytoplasm, nucleus, membrane, lysosome, Golgi apparatus, or mitochondria. Typically the additional detection reagent comprises a protein or a fluorophore or both.

The fluorescent signal of the stains of the present invention and the detectable response of the additional detection reagent may be observed simultaneously or sequentially. The observation of mitochondrial staining and a detectable response that are spatially coincident indicate that the additional detection reagent is associated with the mitochondria of the sample (Examples 20–23). A variety of measurements can be made within mitochondria in this manner, even when the additional detection reagent does not itself localize selectively within the mitochondria.

One class of appropriate additional detection reagents is fluorescent nucleic acid stains. A wide variety of appropriate nucleic acid stains are known in the art, including but not limited to, thiazole orange, ethidium homodimer, propidium iodide, Hoechst 33258, and DAPI. Additional useful nucleic acid stains are described in the international applications WO 93/06482, DIMERS OF UNSYMMETRICAL CYANINE DYES published Apr. 1, 1993); U.S. Pat. No. 5,436,134 to Haugland et al., 1995; U.S. Pat. No. 5,321,130 to Yue et al, 1994; U.S. Pat. No. 5,410,030 to Yue et al., 1995; or U.S. Pat. No. 5,437,980 to Haugland et al., 1995. The use of an appropriate nucleic acid stain in conjunction with the dyes of the present invention can be selected to allow simultaneous observation of nuclear DNA, cellular RNA and/or mitochondrial DNA. Of particular utility is an additional detection reagent that is a cell-permeant nucleic acid stain, such as those described in U.S. Pat. No. 5,436,134, allowing simultaneous visualization of mitochondria and the cellular DNA and RNA, including DNA present in the cell nucleus. Alternatively, the nucleic acid stain used is a stain that is impermeant to live cells and has fluorescence that contrasts with that of the cell or mitochondrial stain used. For green fluorescent stains of the invention, such contrasting stains include propidium iodide and ethidium homodimer, where the red fluorescent nucleus that results from the contrasting stain indicates that the cell membrane is compromised. Similarly, red fluorescent mitochondrial stains can combined with green nuclear stains such as TO-PRO 1, YO-PRO 1, TOTO 1, YOYO 1, or SYTOX dyes (Molecular Probes, Eugene, Oreg.).

Other appropriate additional detection reagents include selected fluorescent pH or metal ion indicators such as those described in U.S. Pat. No. 5,453,517 to Kuhn et al. (1995), or U.S. Pat. No. 5,405,975 to Kuhn et al. (1995); or in Haugland, supra, 1992 HANDBOOK, Sets 20–22 (incorporated by reference).

In another embodiment of the invention, an appropriate additional detection reagent is any probe that selectively stains a cellular organelle such as the cell membrane, nucleus, Golgi apparatus, endoplasmic reticulum, lysosomes, or is a second mitochondrial stain, such as rhodamine 123, or the fixable mitochondrial stains described in U.S. Pat. No. 5,459,268 to Haugland et al. (1995) (hereby incorporated by reference), or another stain of the invention.

Specific examples of additional detection reagents include stains for acidic organelles, such as LYSOTRACKER (Molecular Probes, Eugene, Oreg.) and other stains for lysosomes described in Copending Application STAINS FOR ACIDIC ORGANELLES, Application SEr. No. 08/544,226 by Zhang et al., filed Oct. 17, 1995 (incorporated by reference). The use of stains that are selective for lysosomes in combination with the stains of the present invention allows multiple color visualization of the mitochondria and acidic organelles in cells (Example 21).

In one embodiment, the additional detection reagent comprises: a) one member of a specific binding pair or a series of specific binding pairs, and b) a means for producing a detectable response. A specific binding pair member can be a ligand or a receptor. Ligands and receptors are complementary members of a specific binding pair, each specific binding pair member having an area on the surface or in a cavity which specifically binds to and is complementary with a particular spatial and polar organization of the other. Ligands for which naturally occurring receptors exist include natural and synthetic peptides and proteins, including avidin and streptavidin, antibodies, enzymes, and hormones; nucleotides and natural or synthetic oligonucleotides; lipids; polysaccharides and carbohydrates; lectins; and a variety of drugs, including therapeutic drugs and drugs of abuse and pesticides.

The additional detection reagent also incorporates a means for producing a detectable response. A detectable response means a change in, or occurrence of, a parameter in a test system which is capable of being perceived, either by direct observation or instrumentally, and which is a function of the presence of a specifically targeted member of a specific binding pair in a cell sample. Such detectable responses include the change in, or appearance of, color, fluorescence, reflectance, pH, chemiluminescence, infrared emission, or the deposition of an electron-rich substrate for visualization by electron microscopy. Appropriate labels to provide a detectable response include, but are not limited to, a visible or fluorescent dye, an enzyme substrate that produces a visible or fluorescent precipitate upon enzyme action (for example, the action of horseradish peroxidase upon diaminobenzidine), an enzyme substrate that produces fluorescence or visible color upon enzymic conversion, visible or fluorescent labeled latex microparticles, or a signal that is released by the action of light upon the reagent (e.g. a caged fluorophore that is activated by photolysis, or the action of light upon diaminobenzidine).

The additional detection reagent may be used in conjunction with enzyme conjugates to localize cellular receptors; to localize hybridization probes; or to probe cells and tissues that do not express the enzyme, for example, by enzyme-linked immunosorbent assay (ELISA), or enzyme-mediated histochemistry or cytochemistry, or other enzyme-mediated techniques. Enzyme-mediated techniques take advantage of the attraction between specific binding pairs to detect a variety of analytes. The additional detection reagent optionally comprises an enzyme substrate as the means to produce a fluorescent precipitate in the presence of the appropriate enzyme, as described in U.S. Pat. No. 5,316,906 to Haugland et al. (1994) and U.S. Pat. No. 5,443,986 to Haugland et al. (1995).

Observation/Analysis

At any time after the sample has been stained, the sample is observed with means for detecting the detectable response of fluorescent staining. In one embodiment, observation is accomplished using visible light microscopy, including confocal microscopy. The sample is typically observed as soon as staining is evident, particularly with live cells, although observation may be delayed with appropriate protection of the sample. Stained cells are optionally observed after the additional steps of fixation and permeabilization. Fixed cells can be air-dried and mounted in acrylic mounting media, according to procedures generally known in the art, without loss of signal. Observation of the sample requires illuminating the stained sample with a wavelength of light appropriate to generate a fluorescent response.

Optionally, the sample is analyzed using instrumentation. For example, analysis of cells is accomplished by illuminating the stained cells with a wavelength of light appropriate to generate a fluorescent response, and electronically detecting and optionally quantifying the fluorescent emission of the stained cells or mitochondria using an appropriate instrument, such as a fluorometer, fluorescent multi-well plate reader, or a flow cytometer. The use of a flow cytometer optionally includes isolating cells by "sorting" based on their fluorescent response.

Any observation or analysis optionally includes the observation or analysis of an additional detection reagent present in the sample, by means generally understood in the art and appropriate for the additional detection reagent utilized.

The examples below are given so as to illustrate the practice of this invention. They are not intended to limit or define the entire scope of this invention.

EXAMPLES

Example 1

Preparation of 5,6-dichloro-2-methylbenzimidazole (Compound 1)

The following compound is prepared:

A mixture of 4,5-dichloro-1,2-phenylenediamine (25 g, 0.14 mol) and a catalytic amount of p-toluenesulfonic acid suspended in toluene (200 mL) is heated to reflux in a 500 mL three-necked flask fitted with a reflux condenser and addition funnel. Triethyl orthoacetate (23 g, 0.14 mol) is added dropwise over the course of 2 hours. The reflux condenser is then replaced with a distillation head and approximately 50 mL of solvent (mixture of ethanol and toluene) is collected. The remaining reaction mixture is allowed to stand at room temperature overnight. The resulting solid is collected by suction filtration and dried under vacuum for 24 hrs. The product is used without further purification.

Example 2

Preparation of 5,6-dichloro-1,2-dimethylbenzimidazole (Compound 2)

The following compound is prepared:

To a stirred solution of 1 (1.0 g, 5.0 mmol) in 10 mL DMF is added methyl iodide (0.7 g, 5.0 mmol). After 5 hrs of stirring at approximately 80° C., the solution is poured into a saturated $NaHCO_3$ solution. The resulting mixture is extracted three times with ethyl acetate (3×50 mL). The combined organic layer is washed with brine and dried over anhydrous sodium sulfate. The resulting solution of crude product is evaporated to dryness under vacuum and then purified using column chromatography on silica gel using 10% $MeOH/CHCl_3$ as eluant.

Example 3

Preparation of 1-(4-chloromethylbenzyl)-5,6-dichloro-2,3-dimethylbenzimidazolium chloride (Compound 3)

The following compound is prepared:

A solution of Compound 2 (0.5 g, 2.3 mmol), a large excess of α,α'-xylylenedichloride and N,N-diisopropylethylamine in DMF is stirred at 100° C. for 5 hours. The reaction mixture is then cooled to room temperature and poured into water. The product is extracted with ethyl acetate, and the combined organic layers are washed with brine then dried over anhydrous sodium sulfate. Evaporation of the solvent gives the product as a light brown solid.

Example 4

Preparation of 5,6-dichloro-1,3-di-(4-chloromethylbenzyl)-2-methylbenzimidazolium chloride (Compound 4)

The following compound is prepared:

A solution of Compound 1 (1 g, 4.6 mmol), one equivalent of N,N-diisopropylethylamine and a large excess of α,α'-xylylenedichloride in DMF is stirred at 100° C. for several hours, then cooled to room temperature. Diethyl ether is added to precipitate the product. The crude product is collected by suction filtration. The resulting solid is resuspended in water (10 mL) and stirred briefly, followed by suction filtration and washing with water. The product is then dried using a vacuum oven to yield a colorless solid. The product is used without further purification.

Example 5

Preparation of 1,3-diethyl-5,6-difluoro-2-methylbenzimidazolium iodide (Compound 5)

The following compound is prepared:

Five grams of 4,5-difluoro2-nitroaniline is hydrogenated in the presence of Pd/C to give 4,5-difluoro-1,2-phenylenediamine, which is then converted to 5,6-difuoro-2-methylbenzimidazole using the method of Example 1. A solution of 5,6-difluoro-2-methylbenzimidazole and 10 equivalents of iodoethane in DMF is stirred at 100° C. for about 5 hours. After the reaction mixture has cooled to room temperature, the product is precipitated by the addition of diethyl ether. The precipitate is collected by suction filtration, and then resuspended in water, followed by brief stirring. The solid is collected again by suction filtration and dried at 50° C. under vacuum.

Example 6

Preparation of 2-(2-anilinovinyl)-1-methylbenzoxazolium iodide (Compound 6)

The following compound is prepared:

A solution of 2,3-dimethylbenzoxazolium iodide (1.0 g) and one equivalent of N,N'-diphenylformamidine in 15 mL acetic anhydride is heated at reflux for 1 hr. After the reaction has cooled to room temperature, the product is precipitated by the addition of diethyl ether. The product is collected by suction filtration and then dried under vacuum.

Example 7

Preparation of Compound 7

The following compound is prepared:

A 1:1 mixture of 2,3-dimethylbenzoxazolium iodide and malonaldehyde dianil hydrochloride in acetic acid is heated at reflux for three hours. The resulting reaction mixture is cooled to room temperature and the solvent is removed by rotary evaporation. The resulting gummy yellow solid is redissolved in DMF, followed by the addition of one equivalent each of Compound 4, N,N-diisopropylethylamine, and acetic anhydride. The resulting solution is stirred at room temperature for 24 hours. The resulting purple red solution is poured into a saturated NaCl solution. The resulting precipitate is collected by suction filtration and then dried under vacuum. The crude product is purified using column chromatography on silica gel using MeOH/CHCl₃ as eluant.

Example 8

Preparation of Compound 8

The following compound is prepared:

5,6-Dichloro-2-methyl-1,3-di-(4-methylbenzyl) benzimidazolium chloride is prepared from 1 and 4-methylbenzyl chloride using the procedure described in Example 4. The benzimidazolium derivative (0.5 g) and one equivalent each of 6 and N,N-diisopropylethylamine are mixed in DMF (10 mL) and then stirred for 24 hours. The title compound is isolated using the procedure described in Example 16.

Example 9

Preparation of 1,3-diethyl-2,5,6-trimethylbenzimidazolium iodide (Compound 9)

The following compound is prepared:

2,5,6-Trimethylbenzimidazole is prepared from 4,5-dimethyl-1,2-phenylenediamine and triethylorthoacetate using the procedure described in Example 1. The resultant 2,5,6-trimethylbenzimidazole (5 g, 36.3 mmol) and iodoethane (22.6 g, 145 mmol) are dissolved in 25 mL DMF. The solution is stirred at 100° C. for 5 hours and then cooled to room temperature. Diethyl ether (50 mL) is added to precipitate the product, which is collected by suction filtration. The precipitate is suspended in 10 mL water and stirred briefly, followed by suction filtration and drying at 50° C. under house vacuum for 24 hours.

Example 10

Preparation of 5,6-dichloro-2,3-dimethyl-1-(3-chloro-2-oxopropyl)benzimidazolium chloride (Compound 10)

The following compound is prepared:

A mixture of (0.5 g, 2.3 mmol), 1,3-dichloroacetone (5 mL) and N,N-diisopropylethylamine (0.3 mL) in 10 mL DMF is stirred at 100° C. for 5 hours. The solution is cooled to room temperature and then poured into 50 mL diethyl ether. The precipitate is collected by suction filtration and then suspended in water (10 mL), followed by brief stirring. The precipitate is collected again by suction filtration and dried at 50° C. under house vacuum for 24 hours.

Example 11

Preparation of 2-nitro-4-trifluoroaniline (Compound 11)

The following compound is prepared:

To a solution of 4-trifluoromethylaniline (10 g, 62 mmol) in 50 mL acetic acid cooled at 0° C. is added dropwise 1.2 equivalents of concentrated nitric acid. The resulting solution is stirred for one hour at 0° C., and then warmed to room temperature and stirred overnight. The reaction solution is then neutralized with a saturated NaHCO₃ solution and extracted with chloroform. The combined organic fractions are washed with brine and dried over anhydrous sodium sulfate. Evaporation of the solvent gives the crude product, which is further purified using column chromatography on silica gel using MeOH/CHCl₃ as eluant.

Example 12

Synthesis of 2-mercapto-5-trifluoromethylbenzimidazole (Compound 12)

The following compound is prepared:

A solution of Compound 11 (5.0 g, 24.3 mmol) in methanol is hydrogenated in the presence of Pd/C catalyst for 1 hour. The catalyst is removed by filtration and the filtrate is evaporated to dryness to give 4-trifluoromethyl-1,2-phenylenediamine. The 4-trifluoromethyl-1,2-phenylenediamine is dissolved in 100 mL dry THF with triethylamine (4.9 g, 48.6 mmol) under an inert atmosphere, and the resulting solution is stirred in a 0° C. bath. One equivalent of thiophosgene is added dropwise over a period of one hour. The resulting solution is stirred at 0° C. for an additional 3 hours and then allowed to warm to room temperature. The solution is stirred at room temperature overnight. The reaction mixture is poured into water and extracted with ethyl acetate three times (3×50 mL). The combined organic layers are washed with brine and dried over anhydrous sodium sulfate. Evaporation of the solvent gives crude Compound 12, which is further purified using column chromatography on silica gel using MeOH/CHCl$_3$ as eluant.

Example 13

Synthesis of 1,3-diethyl-2-ethylthio-5-trifluoromethylbenzimidazolium iodide (Compound 13)

The following compound is prepared:

To a solution of Compound 12 (5.0 g, 23 mmol) in 20 mL DMF is added N,N-diisopropylethylamine (5.93 g, 46 mmol) and 5 equivalents of iodoethane. The solution is stirred at 80° C. for 24 hours. The reaction mixture is then cooled to room temperature and poured into cold water. The resulting precipitate is collected by suction filtration and dried under vacuum to give the desired product.

Example 14

Synthesis of 3-(3-chloro-2-oxopropyl)-2-methylbenzothiazolium chloride (Compound 14)

The following compound is prepared:

A mixture of 2-methylbenzothiazole (10 g) and 40 mL 1,3-dichloroacetone is stirred at 120° C. for 24 hours. The resulting gummy solid is triturated with ethyl acetate several times. The resulting solid is collected by suction filtration and dried under vacuum. The product is used without further purification.

Example 15

Synthesis of Compound 15

The following compound is prepared:

A mixture of Compound 13 (1.0 g, 2.33 mmol), Compound 14 (0.64 g, 2.33 mmol) and N,N-diisopropylethylamine (0.3 g, 2.33 mmol) in DMF (15 mL) is stirred at room temperature overnight. The resulting solution is poured into 50 mL of brine, and the resulting precipitate is collected by suction filtration. The crude product is washed with water and ethyl acetate, and dried under vacuum. The crude product is further purified using column chromatography on silica gel eluting with MeOH/CHCl$_3$.

Example 16

Preparation of Compound 16

The following compound is prepared:

A mixture of Compound 3 (0.5 g) and one equivalent each of 6, N,N-diisopropylethylamine, and acetic anhydride in DMF (10 mL) is stirred at room temperature for 24 hours. The resulting solution is poured into a saturated sodium chloride solution, resulting in an orange precipitate, which is then collected using vacuum filtration. The crude product is then purified by column chromatography on silica gel using MeOH/CHCl$_3$ as eluant.

A compound analogous to Compound 16 but with both nitrogens of benzimidazolium moiety substituted by 4-chloromethylbenzyl (Compound 17) is prepared similarly by combining 6 in a 1:1 ratio with Compound 4 instead of with Compound 3.

Example 17

Comparison of Fluorescence Spectra

Compound 8 is dissolved in methanol to give a stock solution with dye concentration in the millimolar range, and then diluted with methanol to yield a test solution with a dye concentration of 0.5 µM. A stock solution of Rhodamine 123 (Molecular Probes, Eugene, Oreg.) is diluted in methanol to give an equal concentration of dye.

Figure 2:
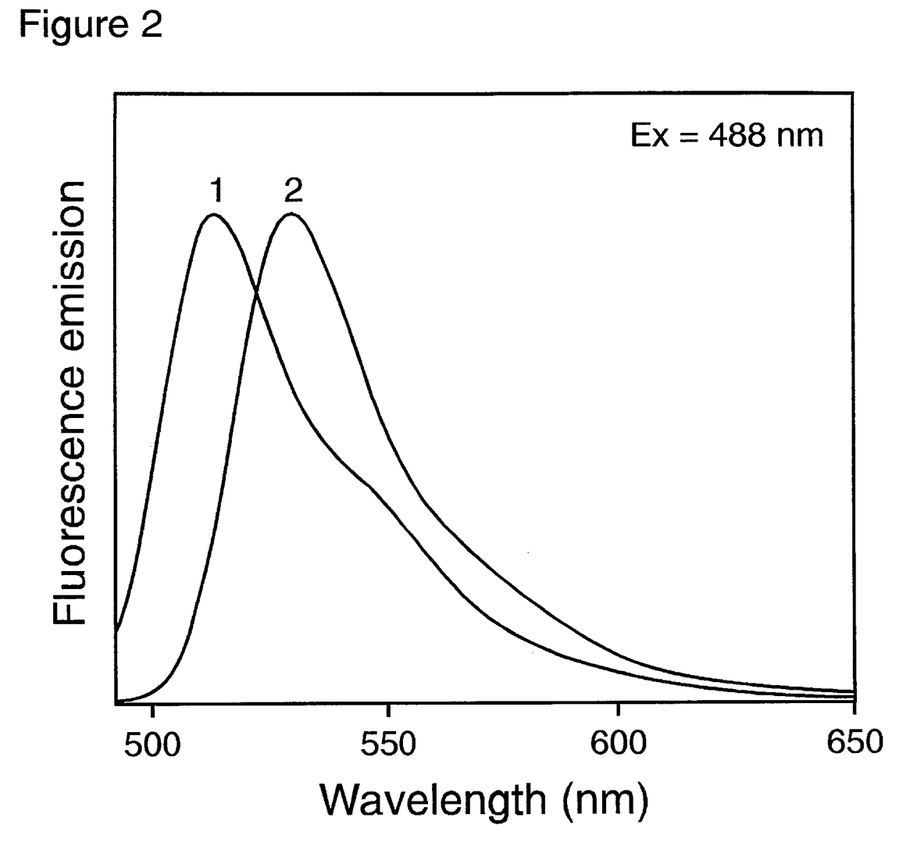
FIG. 2: Normalized fluorescence emission spectra of Compound 8 (1) and rhodamine 123 (2) in methanol (Example 17).

In a spectrophotometer, each solution is excited at 488 nm and the resulting fluorescence emission is recorded from 490–700 nm. The results, normalized for easier comparison, are depicted in FIG. 2. Compound 8 exhibits an emission spectrum that is more blue shifted than the emission spectrum of Rhodamine 123.

Figure 4:
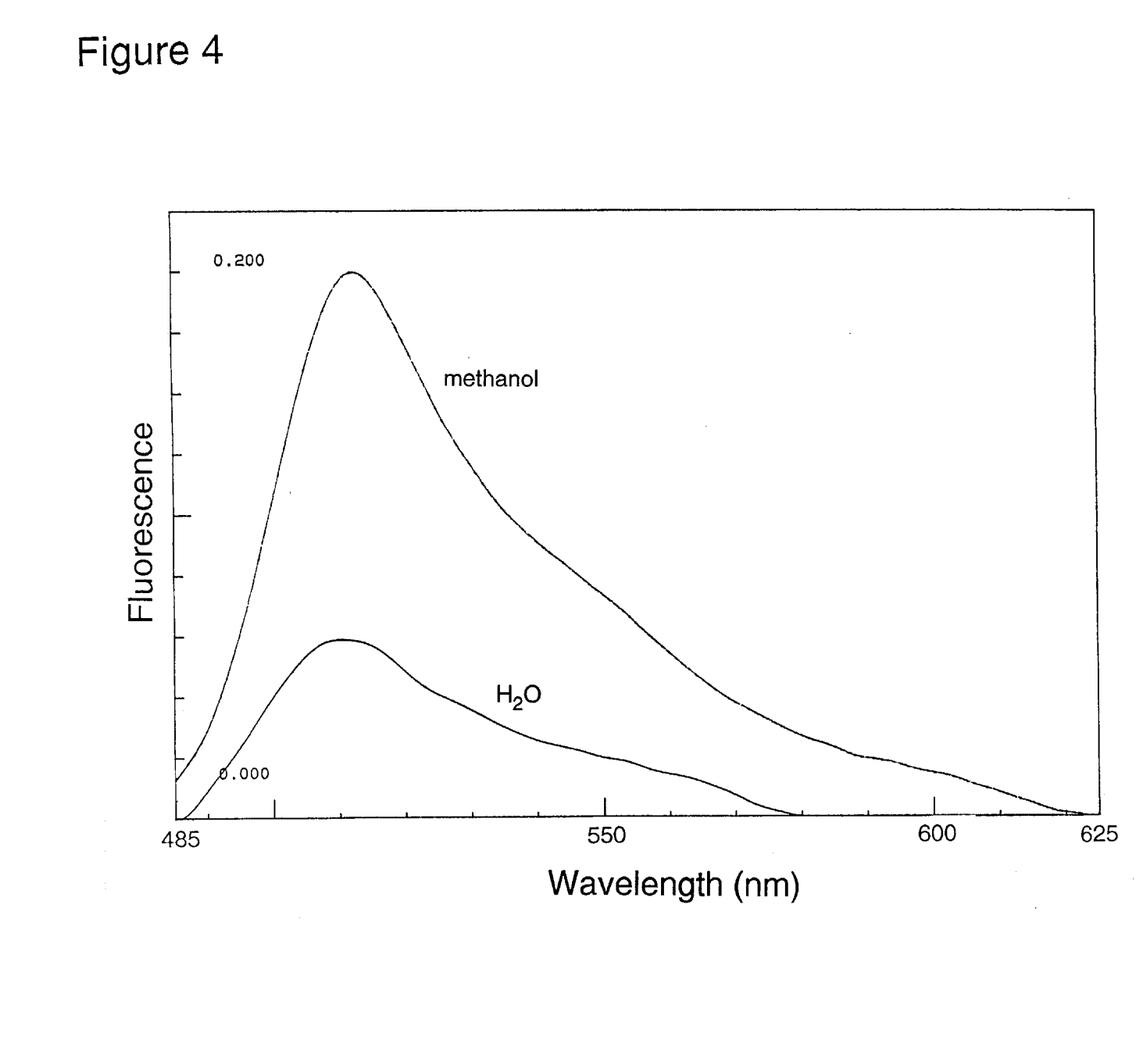
FIG. 4: Fluorescent enhancement of Compound 17 in a lipophilic environment. Fluorescence of Compound 17 is compared in methanol and water (Example 17).

A stock solution of Compound 17 is prepared as above and used to make two test solutions. One is diluted with methanol, the other with water. The optical density of each solution is adjusted to 0.03 when measured at 475 nm. The emission spectra are taken as above over 480–675 nm, and the results are depicted in FIG. 4. The area under the curve indicates relative quantum yield, which is significantly greater in methanol than in water.

Example 18

Comparison of Photostability

HeLa cells are stained with 100 nM Compound B or 500 nM Rhodamine 123 in growth medium for 20 minutes at 37° C. Cells are then rinsed in Hanks Balanced Salt Solution (HBSS) without phenol red and with 10% calf serum and mounted in the same at 37° C. Cells are visualized on a Nikon Diaphot microscope equipped with a 40×/0.75 NA Plan Fluor objective lens, a longpass fluorescein filter (Omega XF25), a Star-1 cooled CCD camera (Photometrics, Tucson, Ariz., and image acquisition software (Image-1, Universal Imaging, West Chester, Pa.). Samples are continuously illuminated for 100 seconds with one image acquired every 5 seconds; integration time is 0.2 seconds with the camera gain set on 4 (FIG. 3). Based on the quantitative data from the measurement, the photobleaching rate of rhodamine 123 is more than eight times higher than that of Compound 8 in the first 100 seconds in living cells. Compound 8 is advantageous for cell biologists because the strong green fluorescence of stained mitochondria lasts long enough so that the image can be photographed.

Example 19

Mitochondrial Specific Staining

NIH/3T3 mouse fibroblast cell line (American Type Culture Collection Co., Rockille, Md.) are maintained in a humidified atmosphere of 5% $CO_2$ in Dulbecco's modified Eagle's medium (DMEM) supplemented with 10% calf serum, 50 µg/mL gentamicin, 300 µg/mL L-glutamine and 10 mM HEPES pH 7.4, and subcultured every 3 days by trypsinization using 0.05% trypsin and 0.02% EDTA in a Ca- and Mg-free saline solution (Gibco BRL, Gaithersburg, Md.). To obtain well-spread single cells, $5 \times 10^4$ cells are plated onto 18×18 mm coverslips in 60-mm culture dishes. The cells are incubated in 100 nM Compound 8 or 17 for 15 to 30 min. Cells are then washed with fresh medium before examination. Cells are observed using a Zeiss Axioplan microscope equipped with a filter optimized for fluorescein. Green fluorescence of all the cells in each of the dye-containing media is limited to the mitochondria only.

After being transferred to fresh medium, Compound 17 remained in the mitochondria of the cells for 48 hours at 37° C. and Compound 8 remained in mitochondria for 16 hours. In. comparison, rhodamine 123 leaks out of cells within 2 hours after the cells are transferred to fresh medium.

Example 20

Colocalization of Two Mitochondrial Stains

Human lung fibroblasts (MRC-5) are grown on coverslips and stained with 100 nM of Compound 17 and 100 nM of the mitochondrial stain CMXRos (Molecular Probes, Eugene, Oreg.) in culture medium for 30 minutes at 37° C. Coverslips are inverted onto a slide in a drop of culture medium, the coverslip is sealed onto the slide with molten wax, and the slide is examined with an epifluorescence microscope equipped with an arc lamp excitation and a triple bandpass filter (for emissions of fluorescein and TEXAS RED dyes) or with a 515 nm longpass filter. Where both fluorochromes coincide, yellow fluorescence is observed; at locations where only one of the fluorochromes occur, green or red fluorescence is observed. Cells exhibit yellow fluorescent "worm-like" structures; no isolated red or green structures are observed, showing that Compound 17 fully co-localizes with the mitochondrial stain CMXRos.

Example 21

Multicolor Labeling of Mitochondria and Other Organelles

Cells prepared according to Example 19 are transferred to the labeling solution containing 100 nM Compound 17 and 50 nM LYSOTRACKER RED (Molecular Probes, Eugene, Oreg.) and incubated at 37°C. for 20 to 60 minutes. The cells are then washed with pre-warmed fresh medium and observed using a Zeiss Axioplan microscope equipped with an appropriate filter set. The stained cells display green mitochondria and red acidic organelles.

Incubating the cells at 37° C. for 30 minutes in a labeling solution that is 100 nM Compound 17, 100 nM BODIPY TR labeled ceramide (Molecular Probes, Eugene, Oreg.) and 30 nM Hoechst 33258 Molecular Probes, Eugene, Oreg.), followed by washing and examining as above, gives green fluorescent mitochondria, red fluorescent Golgi and blue fluorescent nuclei.

Example 22

Colocalization of Mitochondrial Staining with a Labeled Antibody

Human lung fibroblasts (MRC-5) are grown on coverslips and stained with 100 nM of Compound 17 in culture medium for 30 minutes at 37° C. and rinsed with Hank's balanced salt solution (HBSS) at 37° C. The cells are fixed in 3.7% formaldehyde in HBSS at 37° C. for 10 minutes, rinsed 3 or 4 times with HBSS at room temperature, permeabilized in acetone at −20° C. for 10 minutes, and rehydrated in HBSS at room temperature for 10 minutes. Coverslips are then incubated for 30 minutes at room temperature in a blocking solution (1% serum albumin, 1% normal goat serum, and 0.1% TWEEN-20 in phosphate buffered saline), subsequently incubated with 60 µg/mL of a mouse antibody raised against the human cytochrome oxidase subunit I (diluted in blocking solution) for one hour. Coverslips with cells are then washed once in phosphate buffered saline and incubated with 10 µg/mL of a TEXAS RED-X fluorophore conjugated goat anti-mouse secondary antibody diluted in blocking solution. Coverslips with cells are rinsed again in phosphate buffered saline, air dried, mounted in acrylic mounting resin and viewed by epifluorescence microscopy. Cells exhibit yellow fluorescent "worm-like" structures with no isolated red or green structures, showing that the dye is localized coincident with the labeled antibody at the mitochondria. The cells being permeabilized for antibody labeling, may also be fixed prior to mitochondrial staining according to Example 24 below.

Example 23

Detection of Foreign Gene Product in Mitochondria

Following the procedure of Example 22, stained mitochondria in fixed and permeabilized cells are incubated with labeled antibodies directed against a specific amino acid sequence from a mitochondrial targeted polypeptide that results from a transfected gene sequence. Since the green fluorescence staining of mitochondria is well-defined and clearly observable, the immunocomplexes are shown to be localized in mitochondria.

Example 24

Staining of Fixed Cells

Bovine pulmonary artery endothelial cells (BPAEC) are grown on coverslips and treated for 10 minutes with ice-cold absolute methanol at −20° C. temperature. Coverslips are rinsed twice in phosphate buffered saline, rehydrated in phosphate buffered saline for 10 minutes at room temperature, and stained with 100 nM of Compound 17 in phosphate buffered saline for 30 minutes at room temperature; rinsed with phosphate buffered saline at room temperature, and are viewed by epifluorescence microscopy. Cells show bright green fluorescent staining of mitochondria.

Example 25

Insensitivity of Staining to Perturbation of Mitochondrial Function

Cultures of human lymphoid cell lines (LCLs) are maintained at logarithmic growth in RPMI-1640 culture medium supplemented with 10% fetal bovine serum, 50 μg gentamycin, and 300 μg L-glutamine per mL of culture medium. In the same culture medium, cells are exposed for 15 minutes at 37° C. to 20 M of rotenone (an inhibitor of respiration complex I), to 20 μM of antimycin (an inhibitor of respiration complex II), or to 20 μM of carbonyl cyanide m-chlorophenylhydrazone (CCCP; an uncoupler of mitochondrial respiration). In the presence of the inhibitors, Compound 17 from a 0.2 mM stock solution in DMSO is added to obtain a final dye concentration on 100 nM. Cells are incubated at 37° C. for another 15 minutes. Fluorescence of cells is analyzed with a flow cytometer equipped with an argon laser set at 100 mW output for the 488 nm line. The forward (low angle) light scatter signal amplification is set such that signals appear in the upper half of the signal detection range. The acquisition trigger logic of the instrument is set on the fluorescence detector collecting light around 530 nm (the "fluorescein detector"). The signal amplification rate of said detector is set such that signals from the sample under investigation emerge within the detection range. Fluorescence resulting from Compound 17 appears independent of pre-treatment with the inhibitors of mitochondrial function.

| Dye | Rotenone | Antimycin | CCCP |
|---|---|---|---|
| CMXRos | 113 ± 9 | 49 ± 5 | 48 ± 9 |
| Compound 17 | 108 ± 9 | 84 ± 7 | 115 ± 3 |
| NAO[†] | 117 ± 5 | 88 ± 8 | 82 ± 11 |

[†]NAO is nonyl acridine orange (Molecular Probes, Eugene, OR), a membrane-potential independent mitochondrial stain.

It is to be understood that, while the foregoing invention has been described in detail by way of illustration and example, numerous modifications, substitutions, and alterations are possible without departing from the spirit and scope of the invention as described in the following claims.

What is claimed is:
1. A compound having the formula wherein
each of $R^1$, $R^2$, and $R^3$ is independently a linear hydrocarbon that is saturated or unsaturated, has 1–22 carbons, optionally incorporates a 5- or 6-membered unsaturated hydrocarbon ring, and is optionally substituted by one or more halogens; provided that at least one of $R^1$, $R^2$, and $R^3$ is substituted by wherein
Z is selected from the group consisting of Cl, Br and I;
$R^a$ and $R^b$ are selected from the group consisting of H and $CH_3$;
X is halogen; and
$R^c$ is selected from the group consisting of alkyl having 1–6 carbons; perfluoroalkyl having 1–6 carbons; and phenyl that is optionally substituted one or more times by alkyl having 1–6 carbons, perfluoroalkyl having 1–6 carbons, H, Cl, Br, I, $NO_2$ or CN;
$R^4$, $R^5$, $R^6$, and $R^7$ are independently H, halogen, CN, phenyl, $—OR^{12}$ or $—SR^{12}$; an alkyl group having 1–22 carbons that is optionally and independently substituted by one or more halogens; or any two adjacent substituents of $R^4$, $R^5$, $R^6$, and $R^7$ in combination form a single fused benzo substituent; where $R^{12}$ is an alkyl group having 1–6 carbons, or 1–2 alicyclic, heteroalicyclic, aromatic or heteroaromatic rings, containing 1–2 heteroatoms, wherein the heteroatoms are N, O, or S;
$R^8$, $R^9$, $R^{10}$ and $R^{11}$ are independently H, halogen, CN, phenyl, $—OR^{15}$ or $—SR^{15}$; an alkyl group having 1–22 carbons that is optionally and independently substituted by one or more halogens; or any two adjacent substituents of $R^8$, $R^9$, $R^{10}$ and $R^{11}$ in combination form a single fused benzo substituent; where $R^{15}$ is an alkyl group having 1–6 carbons, or 1–2 alicyclic, heteroalicyclic, aromatic or heteroaromatic rings, containing 1–2 heteroatoms, wherein the heteroatoms are N, O, or S;

W is selected from O, S, Se, Te or $CR^{13}R^{14}$ where $R^{13}$ and $R^{14}$, which may be the same or different, are independently alkyl groups having 1–6 carbons, or $R^{13}$ and $R^{14}$ taken in combination complete a five or six membered saturated ring;

n=0–3; and $\Psi^-$ is a biologically compatible counterion.

2. A compound as claimed in claim 1, wherein W is O or S or $CR^{13}R^{14}$.

3. A compound as claimed in claim 1, wherein n=1.

4. A compound as claimed in claim 1, wherein $R^5$ and $R^6$ are halogen, and $R^4$ and $R^7$ are H; and $R^8$ through $R^{11}$ are independently H, halogen, or alkyl having 1–6 carbons.

5. A compound, as claimed in claim 1, wherein W is O or S or $CR^{13}R^{14}$; and n=1; and $R^5$ and $R^6$ are H or halogen, or alkyl that is optionally substituted by one or more H or halogen; and $R^4$ and $R^7$ are H; and $R^8$ through $R^{11}$ are independently H, halogen, or methyl.

6. A compound, as claimed in claim 5, wherein at least one of the linear hydrocarbons $R^1$, $R^2$ and $R^3$ has 7–10 carbons.

7. A compound, as claimed in claim 5, wherein at least one of the linear hydrocarbons $R^1$, $R^2$ and $R^3$ has more than 10 carbons.

8. A compound, as claimed in claim 5, wherein at least one of the linear hydrocarbons $R^1$, $R^2$ and $R^3$ has 1–6 carbons.

9. A compound, as claimed in claim 1, wherein at least one of the linear hydrocarbons $R^1$, $R^2$ and $R^3$ is substituted by wherein $R^a$ and $R^b$ are selected from the group consisting of H and $CH_3$;

X is halogen; and $R^c$ is selected from the group consisting of alkyl having 1–6 carbons; perfluoroalkyl having 1–6 carbons; and phenyl that is optionally substituted one or more times by alkyl having 1–6 carbons, perfluoroalkyl having 1–6 carbons, H, Cl, Br, I, $NO_2$ or CN.

10. A compound as claimed in claim 1, wherein at least one of $R^1$, $R^2$ or $R^3$ is -continued where X is halogen.

11. A compound, as claimed in claim 1, wherein $R^5$ and $R^6$ are halogen;

$R^4$ and $R^7$ are H;

$R^8$ through $R^{11}$ are independently H, halogen, or alkyl having 1–6 carbons; and $R^1$ and $R^2$ are both or $R^1$ and $R^2$ are both

12. A method of staining cells, comprising:

incubating a sample containing cells with a mostly aqueous staining solution comprising a cyanine compound of the formula wherein each of $R^1$, $R^2$, and $R^3$ is independently a linear hydrocarbon that is saturated or unsaturated, has 1–22 carbons, optionally incorporates a 5- or 6-membered unsaturated hydrocarbon ring, and is optionally substituted by one or more halogens; provided that at least one of $R^1$, $R^2$, and $R^3$ is substituted by wherein Z is selected from the group consisting of Cl, Br, and I;

$R^a$ and $R^b$ are selected from the group consisting of H and $CH_3$;

X is halogen; and $R^c$ is selected from the group consisting of alkyl having 1–6 carbons; perfluoroalkyl having 1–6 carbons; and phenyl that is optionally substituted one or more times by alkyl having 1–6 carbons, perfluoroalkyl having 1–6 carbons, H, Cl, Br, I, $NO_2$ or CN;

$R^4$, $R^5$, $R^6$, and $R^7$ are independently H, halogen, CN, phenyl, $-OR^{12}$ or $-SR^{12}$; an alkyl group having 1–22 carbons that is optionally and independently substituted by one or more halogens; or any two adjacent substituents of $R^4$, $R^5$, $R^6$, and $R^7$ in combination form a single fused benzo substituent; where $R^{12}$ is an alkyl group having 1–6 carbons, or 1–2 alicyclic, heteroalicyclic, aromatic or heteroaromatic rings, containing 1–2 heteroatoms, wherein the heteroatoms are N, O, or S;

$R^8$, $R^9$, $R^{10}$ and $R^{11}$ are independently H, halogen, CN, phenyl, $-OR^{15}$ or $-SR^{15}$; an alkyl group having 1–22 carbons that is optionally and independently substituted by one or more halogens; or any two adjacent substituents of $R^8$, $R^9$, $R^{10}$ and $R^{11}$ in combination form a single fused benzo substituent; where $R^{15}$ is an alkyl group having 1–6 carbons, or 1–2 alicyclic, heteroalicyclic, aromatic or heteroaromatic rings, containing 1–2 heteroatoms, wherein the heteroatoms are N, O, or S;

W is selected from O, S, Se, Te or $CR^{13}R^{14}$ where $R^{13}$ and $R^{14}$, which may be the same or different, are independently alkyl groups having 1–6 carbons, or $R^{13}$ and $R^{14}$ taken in combination complete a five or six membered saturated ring;

n=0–3; and $\Psi^-$ is a biologically compatible counterion;

where said compound is present in an amount sufficient to selectively accumulate in selected areas of the cells; and the cells are incubated in the staining solution for a time sufficient for the cyanine compound to selectively accumulate in said selected areas of the cells and become fluorescent.

13. A method, as claimed in claim 12, further comprising the step of fixing and optionally permeabilizing cell membranes.

14. A method, as claimed in claim 12, where the cells contain mitochondria.

15. A method, as claimed in claim 14, where the cells are animal cells that are fixed and optionally permeabilized.

16. A method, as claimed in claim 12, further comprising adding an additional detection reagent to the sample, wherein said additional detection reagent is a reagent that produces a detectable response due to the presence of a specific cell component, intracellular substance, or cellular condition.

17. A method, as claimed in claim 12, comprising:

incubating a sample containing cells, which are optionally fixed and optionally permeabilized, for 10 minutes to 1 hour with an aqueous staining solution comprising 20–500 nM of a cyanine compound of the formula:

wherein each of $R^1$, $R^2$, and $R^3$ is independently a linear hydrocarbon that is saturated or unsaturated, has 1–22 carbons, optionally incorporates a 5- or 6-membered unsaturated hydrocarbon ring, and is optionally substituted by one or more halogens; provided that at least one of $R^1$, $R^2$, and $R^3$ is substituted by wherein $R^a$ and $R^b$ are selected from the group consisting of H and $CH_3$; and X is halogen;

$R^4$, $R^5$, $R^6$, and $R^7$ are independently H, halogen, CN, phenyl, $-OR^{12}$ or $-SR^{12}$; an alkyl group having 1–22 carbons that is optionally and independently substituted by one or more halogens; or any two adjacent substituents of $R^4$, $R^5$, $R^6$, and $R^7$ in combination form a single fused benzo substituent; where $R^{12}$ is an alkyl group having 1–6 carbons, or 1–2 alicyclic, heteroalicyclic, aromatic or heteroaromatic rings, containing 1–2 heteroatoms, wherein the heteroatoms are N, O, or S;

$R^8$, $R^9$, $R^{10}$ and $R^{11}$ are independently H, halogen, CN, phenyl, $-OR^{15}$ or $-SR^{15}$; an alkyl group having 1–22 carbons that is optionally and independently substituted by one or more halogens; or any two adjacent substituents of $R^8$, $R^9$, $R^{10}$ and $R^{11}$ in combination form a single fused benzo substituent; where $R^{15}$ is an alkyl group having 1–6 carbons, or 1–2 alicyclic, heteroalicyclic, aromatic or heteroaromatic rings, containing 1–2 heteroatoms, wherein the heteroatoms are N, O, or S;

W is selected from O, S, or $CR^{13}R^{14}$ where $R^{13}$ and $R^{14}$, which may be the same or different, are independently alkyl groups having 1–2 carbons;

n=0–2; and $\Psi^-$ is a biologically compatible counterion.

18. A method of staining mitochondria or a mitochondrial component, comprising: incubating a sample that contains mitochondria or an isolated mitochondrial component with an aqueous miscible staining solution comprising a cyanine compound of the formula:

wherein
each of $R^1$, $R^2$, and $R^3$ is independently a linear hydrocarbon that is saturated or unsaturated, has 1–22 carbons, optionally incorporates a 5- or 6-membered unsaturated hydrocarbon ring, and is optionally substituted by one or more halogens; provided that at least one of $R^1$, $R^2$, and $R^3$ is substituted by wherein
Z is selected from the group consisting of Cl, Br and I;
$R^a$ and $R^b$ are selected from the group consisting of H and $CH_3$;
X is halogen; and
$R^c$ is selected from the group consisting of alkyl having 1–6 carbons; perfluoroalkyl having 1–6 carbons; and phenyl that is optionally substituted one or more times by alkyl having 1–6 carbons, perfluoroalkyl having 1–6 carbons, H, Cl, Br, I, $NO_2$ or CN;
$R^4$, $R^5$, $R^6$, and $R^7$ are independently H, halogen, CN, phenyl, $-OR^{12}$ or $-SR^{12}$; an alkyl group having 1–22 carbons that is optionally and independently substituted by one or more halogens; or any two adjacent substituents of $R^4$, $R^5$, $R^6$, and $R^7$ in combination form a single fused benzo substituent; where $R^{12}$ is an alkyl group having 1–6 carbons, or 1–2 alicyclic, heteroalicyclic, aromatic or heteroaromatic rings, containing 1–2 heteroatoms, wherein the heteroatoms are N, O, or S;
$R^8$, $R^9$, $R^{10}$ and $R^{11}$ are independently H, halogen, CN, phenyl, $-OR^{15}$ or $-SR^{15}$; an alkyl group having 1–22 carbons that is optionally and independently substituted by one or more halogens; or any two adjacent substituents of $R^8$, $R^9$, $R^{10}$ and $R^{11}$ in combination form a single fused benzo substituent; where $R^{15}$ is an alkyl group having 1–6 carbons, or 1–2 alicyclic, heteroalicyclic, aromatic or heteroaromatic rings, containing 1–2 heteroatoms, wherein the heteroatoms are N, O, or S;

W is selected from O, S, and $CR^{13}R^{14}$ where $R^{13}$ and $R^{14}$, which may be the same or different, are independently alkyl groups having 1–6 carbons, or $R^{13}$ and $R^{14}$ taken in combination complete a five or six membered saturated ring;
n=0–1; and
$\Psi^-$ is a biologically compatible counterion;
where said compound is present in an amount sufficient to stain said mitochondria or mitochondrial component; for a time sufficient for the cyanine compound to selectively stain said mitochondria or mitochondrial component.

19. A method of staining, as claimed in claim 18, where the mitochondria are in cells that have been fixed, or permeabilized, or both.

20. A method of staining, as claimed in claim 19, further comprising adding an additional detection reagent to the sample, wherein said additional detection reagent is a reagent that produces a detectable response due to the presence of a specific cell component, intracellular substance, or cellular condition, and wherein said additional detection reagent comprises a protein.

21. A method of staining, as claimed in claim 18, comprising,
incubating a sample containing mitochondria in cells, for 10 minutes to 1 hour with an aqueous miscible staining solution comprising 20–500 nM of a cyanine dye compound of the formula:

wherein
each of $R^1$, $R^2$, and $R^3$ is independently a linear hydrocarbon that is saturated or unsaturated, has 1–22 carbons, optionally incorporates a 5- or 6-membered unsaturated hydrocarbon ring, and is optionally substituted by one or more halogens; provided that at least one of $R^1$, $R^2$, and $R^3$ is substituted by wherein
$R^a$ and $R^b$ are selected from the group consisting of H and $CH_3$; and
X is halogen;
$R^4$, $R^5$, $R^6$, and $R^7$ are independently H, halogen, CN, phenyl, $-OR^{12}$ or $-SR^{12}$; an alkyl group having 1–22 carbons that is optionally and independently substituted by one or more halogens; or any two adjacent substituents of $R^4$, $R^5$, $R^6$, and $R^7$ in combination form a single fused benzo substituent; where $R^{12}$ is an alkyl group having 1–6 carbons;

$R^8$, $R^9$, $R^{10}$ and $R^{11}$ are independently H, halogen, CN, phenyl, —$OR^{15}$ or —$SR^{15}$; an alkyl group having 1–22 carbons that is optionally and independently substituted by one or more halogens; or any two adjacent substituents of $R^8$, $R^9$, $R^{10}$ and $R^{11}$ in combination form a single fused benzo substituent; where $R^{15}$ is an alkyl group having 1–6 carbons;

W is selected from O, S, and $CR^{13}R^{14}$ where $R^{13}$ and $R^{14}$, which may be the same or different, are independently alkyl groups having 1–2 carbons; and n=1; and Ψ⁻ is a biologically compatible counterion.

22. A method of staining, as claimed in claim 21, where for the formula of the cyanine dye compound:

$R^5$ and $R^6$ are independently H, halogen, or an alkyl group having 1–3 carbons that is optionally and independently substituted by one or more H or halogen;

$R^8$, $R^9$, $R^{10}$ and $R^{11}$ are independently H, halogen, CN, phenyl; an alkyl group having 1–3 carbons that is optionally and independently substituted by one or more H or halogen; or —$OR^{12}$ or —$SR^{12}$, where $R^{12}$ is an alkyl group having 1–6 carbons;

$R^4$ and $R^7$ are H; and $R^1$ and $R^2$ both have the formula or $R^1$ and $R^2$ both have the formula where X is halogen.

* * * * *